United States Patent
Thomson

(10) Patent No.: US 7,683,327 B2
(45) Date of Patent: Mar. 23, 2010

(54) DEVELOPMENT OF DISPOSABLE/SEALABLE TIPS FOR SPECTROSCOPIC PROBES

(75) Inventor: Alasdair Iain Thomson, Hull (GB)

(73) Assignee: BP Oil International Limited, Middlesex (GB)

( * ) Notice: Subject to any disclaimer, the term of this patent is extended or adjusted under 35 U.S.C. 154(b) by 36 days.

(21) Appl. No.: 11/922,011

(22) PCT Filed: Jun. 13, 2006

(86) PCT No.: PCT/GB2006/002160

§ 371 (c)(1),
(2), (4) Date: Dec. 12, 2007

(87) PCT Pub. No.: WO2006/136786

PCT Pub. Date: Dec. 28, 2006

(65) Prior Publication Data

US 2008/0283756 A1  Nov. 20, 2008

(30) Foreign Application Priority Data

Jun. 20, 2005  (EP)  .................... 05253809

(51) Int. Cl.
*G01J 5/02* (2006.01)
(52) U.S. Cl. .................. 250/339.11; 250/341.2
(58) Field of Classification Search ............ 250/339.11, 250/338.1, 252.1, 339.12, 341.8, 341.2
See application file for complete search history.

(56) References Cited

U.S. PATENT DOCUMENTS

| | | | |
|---|---|---|---|
| 2,983,820 A * | 5/1961 | Frentrop | 376/109 |
| 5,404,218 A * | 4/1995 | Nave et al. | 356/301 |
| 5,708,273 A * | 1/1998 | VonBargen | 250/341.2 |
| 6,570,654 B2 * | 5/2003 | Jung et al. | 356/419 |
| 2004/0086215 A1 | 5/2004 | Salerno et al. | |
| 2004/0244971 A1 | 12/2004 | Shammai et al. | |

FOREIGN PATENT DOCUMENTS

| | | |
|---|---|---|
| GB | 2 341 925 | 3/2000 |
| JP | 60-224043 | 11/1985 |
| JP | 2-194351 | 7/1990 |

OTHER PUBLICATIONS

International Search Report for PCT/GB2006/002160 mailed Aug. 21, 2006.

* cited by examiner

*Primary Examiner*—David P Porta
*Assistant Examiner*—Faye Boosalis
(74) *Attorney, Agent, or Firm*—Nixon & Vanderhye

(57) ABSTRACT

Sealable cell for obtaining a reflectance spectrum of a liquid sample using a spectroscopic probe having a removable cap wherein the internal wall of the cap comprises at least one groove that allows air to escape from the head of the probe and a liquid sample held within the cap so that accurate spectra can be obtained.

17 Claims, 2 Drawing Sheets

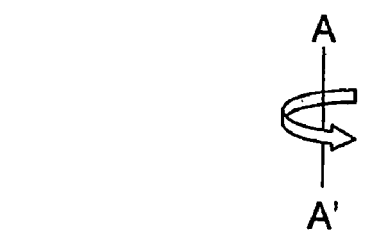
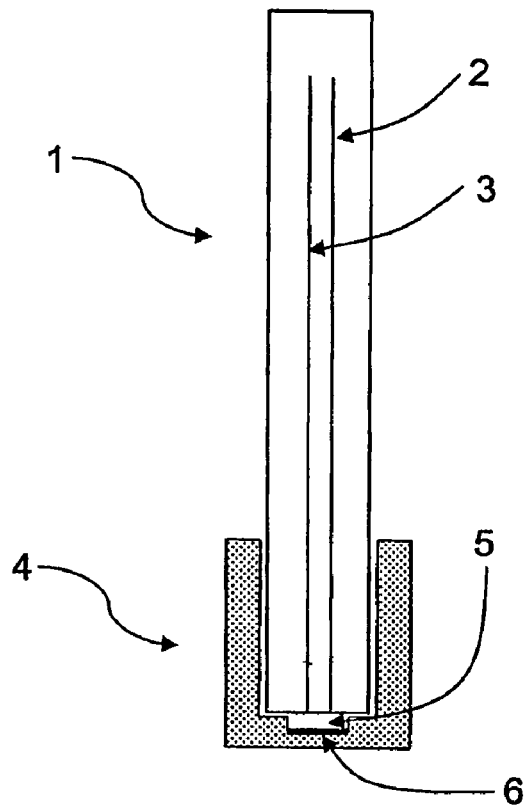
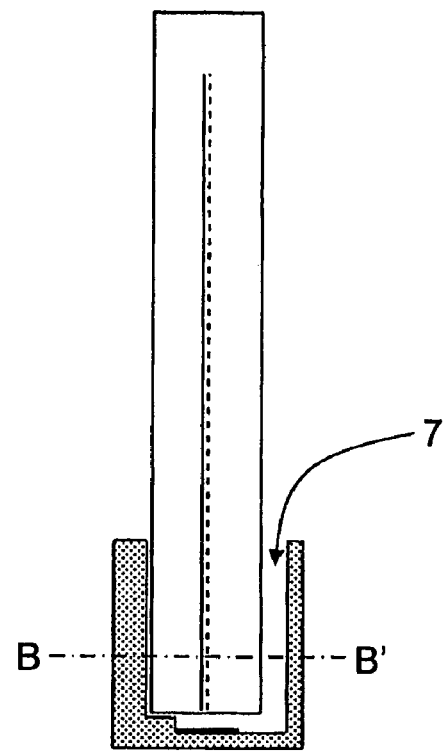
Figure 1
Figure 2
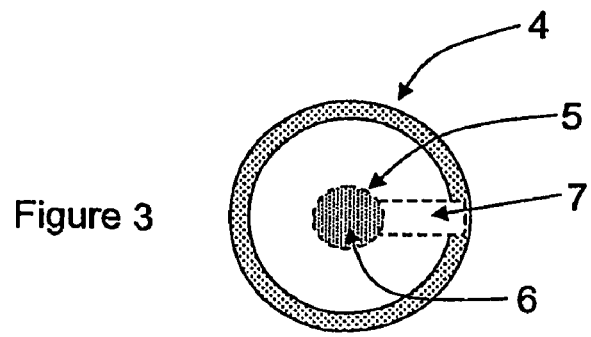
Figure 3

DEVELOPMENT OF DISPOSABLE/SEALABLE TIPS FOR SPECTROSCOPIC PROBES

This application is the U.S. national phase of International Application No. PCT/GB2006/002160 filed 13 Jun. 2006 which designated the U.S. and claims priority to European Patent Application No. 05253809.7 filed 20 Jun. 2005, the entire contents of each of which are hereby incorporated by reference.

The present invention relates to the development of disposable/sealable tips for spectroscopic probes for measuring electromagnetic spectra, particularly near infrared (NIR) spectra.

BACKGROUND OF THE INVENTION

NIR spectroscopy is a well-known spectroscopic technique that looks specifically at the absorptions of infra-red radiation with frequencies of above 4000 $cm^{-1}$. NIR spectroscopy can be used to measure the intensity of the overtones of the molecular vibrations in a molecule, containing carbon-hydrogen, oxygen-hydrogen, and nitrogen-hydrogen bonds. The carbon-hydrogen (C—H) absorption bands are typically useful for mixtures of organic compounds. Different types of C—H bonds, e.g., aromatic, aliphatic, and olefinic hydrocarbons, absorb light at different characteristic frequencies. The magnitude of the absorption band in the spectra is proportional to the number of C—H bonds present in the sample. Hence, NIR spectroscopy is often used to obtain a fingerprint of a sample and by empirically correlating the said fingerprint the intrinsic properties of the sample may also be known.

The NIR region between 780 nanometers (nm) and 2500 nm (12800 to 4000 $cm^{-1}$) is an area of great interest and contains a large amount of molecular information in the form of combinations and overtones from polyatomic vibrations. Mathematical techniques are essential to utilize this information and to calculate the desired properties. U.S. Pat. Nos. 5,490,085; 5,452,232; and 5,475,612, for example, describe the use of NIR for determining octane number, yields and/or properties of a product of a chemical process or separation process from analysis on the feeds to that process, and yields and/or properties of a product of a blending operation again from analysis on the feed thereto.

NIR spectroscopy can be applied to crude oils and other hydrocarbon refinery streams. WO 00/039561 and WO 03/048759, for example, both describe application of NIR to crude oil analysis.

The analysis of crude oil samples, for example, can be performed by generating chemometric models correlating spectral data from "standard" (i.e. characterised) crude oil samples with the known properties of the samples, and subsequently applying said models to the spectra of "unknown" samples to characterise the properties thereof.

"Chemometrics" is the application of mathematical and statistical techniques to the analysis of complex data, and hence "chemometric model" means a model generated from application of such techniques in correlating the spectral data from a sample with properties of the sample and cell pathlength. The chemometric model determines the relationship between the spectral data and the cell pathlength as it would for the chemical and/or physical properties (via eigenvectors of a covariance matrix).

The generation of the chemometric model can be done using any one of a variety of techniques/mathematical and statistical techniques, as described, for example, in Principal Component Analysis, I. T. Jolliffe, Springer-Verlag, New York, 1986; D. M. Halland and E. V. Thomas, Anal. Chem., 60, 1202 (1988) or K. R. Beebe and B. R. Kowalski, Anal. Chem., 59, 1007A (1987).

The analysis of samples such as crude oils is typically done using a transmission cell into which the sample is introduced. The cells typically have a relatively short pathlength so that a reasonable signal is transmitted through the cell. However, such cells require cleaning when used with substances such as crude oils. This is by no means a trivial task when using fixed (solid) cells, so demountable cells are the preferred option. Demountable cells may be disassembled, cleaned and then reassembled again for re-use.

The problem faced with demountable cells, however, is that during the disassembly and reassembly the pathlength of the cell may change. With cells that have a relatively short pathlength, even small changes in the pathlength can have significant effects on the spectra obtained. For example where spectral data from "standard" (i.e. characterised) crude oil samples is being measured for generation of a suitable chemometric model correlating various properties of the crude oil samples with the spectral data, the variations in cell pathlength can have significant detrimental effects on the model obtained.

By convention there are three main types of spectroscopic probes that can be utilised within the aforementioned NIR transmission cells; the transflection (transmission reflection) probe, ATR (attenuated total reflectance probe) and the DRIFTS (Diffuse Reflectance Infrared Fourier Transform Spectroscopy) probe. The transflection probe comprises an NIR probe containing two optical fibres, normally silica, such that light is passed down one fibre which is then projected through a lens/window at the lower end of the probe and reflected—via a mirror—back through the window into the return fibre. A gap between the window and the mirror—the sample support—allows the sample of interest to enter into the light beam and thus an absorption spectrum is obtained.

The DRIFTS probe is similar to the former however there is no mirror present in the probe per se to reflect the light back into the return fibre and as such is normally used to collect spectra from solid samples.

Unfortunately, whilst assembling the transmission cell in order to characterise a sample, as air is present in the optical path, it generates significant inaccuracies in the data obtained.

SUMMARY OF THE INVENTION

The applicants believe that the present invention discloses an apparatus that firstly allows the liquid sample to be sealed within the cell and advantageously maintained at elevated temperatures and pressures and secondly allows the spectroscopic measurement of the liquid samples to be done with a higher degree of accuracy by removing air from the optical path and/or by preventing air from entering into the optical path.

Thus, the present invention relates to a sealable cell for measuring the electromagnetic spectrum of a liquid sample, which cell has a spectroscopic probe and a removable cap, which spectroscopic probe comprises at least one optical fibre, and which removable cap fits over one end of the spectroscopic probe, and has a sample support with a reflecting mirror at its base, wherein the distance between the outer wall of the spectroscopic probe and the inner wall of the disposable cap is less than 0.4 mm, characterised in that; the internal wall of the cap comprises at least one groove that allows a fluid to escape from between the head of the probe and the sample support when the probe is inserted into the removable cap.

According to a preferred embodiment of the present invention the spectroscopic probe comprises two silica optical fibres, one of which allows electromagnetic radiation (e.g. infrared or near infrared radiation) to be transferred from a source to the sample, and another for receiving radiation transmitted and/or reflected from the sample. The probe is preferably cylindrical.

The probe can be made of any appropriate material, preferably metal, more preferably stainless steel. Preferably, the probe is cylindrical, in which the diameter of the cross-section, D, is preferably more than 1.5 mm and less than 30 mm; more preferably more than 6 mm and less than 7 mm; and most preferably more than 6.2 mm and less than 6.6 mm.

The removable cap of the spectroscopic probe comprises a sample support with a reflecting mirror at its base, and at least one—preferably vertically or helically arranged, more preferably vertically arranged—groove(s) along the internal wall of the cap, which groove(s) allows a fluid, for example a liquid sample and/or a gas such as air or any volatile components of a sample, to escape from between the sample and the head of the probe when the probe is inserted into the cap. In a preferred embodiment of the invention, the cap comprises at least one vertically disposed groove on its internal wall which connects the sample support, to the top of the cap, and allows a fluid, such as air or excess liquid sample, to escape from the cell. The groove may have one of many different shapes and configurations, for example having a V-shaped or U-shaped cross-section.

The one or more grooves preferably have a cross-sectional area of at least 0.1 mm$^2$ so as not to restrict the flow of liquids, particularly viscous liquids, to too great an extent. This is because a slower flow of liquid is generally less efficient at removing gases, such as air or volatile components of the sample, from between sample support and the head of the probe. The removable cap can be made of any appropriate material preferably Teflon or a thermoplastic material such as polypropylene or polythene.

The reflecting mirror can be made of any appropriate material preferably aluminium. The sample support, which has the reflecting mirror at its base, preferably takes the form of a depression at the base of the cap, the width or diameter of the depression being narrower than the internal width or diameter of the rest of the cap.

The removable cap is adapted to accommodate at least the head of the probe. The distance between the outer wall of the spectroscopic probe and the inner wall of the disposable cap is less than 0.4 mm. In one embodiment of the invention, the removable cap is narrower than the probe, and is preferably up to 0.4 mm narrower than the probe, more preferably up to 0.2 mm narrower. In this embodiment, the cap is made of a material that can stretch and fit over at least the head of the spectroscopic probe.

Preferably the cap is cylindrical, wherein the internal diameter D' is preferably more than (D−0.4 mm), more preferably more than (D−0.2 mm). The internal diameter D' of the cap is preferably less than (D+0.4 mm), more preferably less than D.

The sample is preferably a liquid sample. The sample may be a hydrocarbon sample, e.g. a crude oil or "equivalent" sample. By "equivalent" sample is meant a sample that may be used either in place of or blended with a crude oil in a refinery, such as a synthetic crude, a biocomponent, an intermediate stream, such as a residue, gas oil, vacuum gas oil, naphtha or cracked stock, and blends of one or more of said components. The present invention is especially useful for measuring liquids that contain volatiles.

Other hydrocarbon samples to which the process of the present invention may be applied include fuels, lubricants, polymers (liquid polymers or polymer melts) and petrochemicals which are prone to fouling.

According to an embodiment of the present invention the spectroscopic measurement begins with a liquid sample occupying the sample support at the base of the removable cap. The spectroscopic probe is then inserted—whilst maintaining contact with the internal walls of the cap—vertically down into the base of the cap until it reaches the top of the sample support, at which point the probe cannot be inserted any further. Gases, such as air or any volatile components in the liquid sample, are forced through a groove(s) on the internal wall of the cap, which extends from the sample support to the top of the cap and provides a means for the gases and any excess liquid sample to escape from the cell, and prevents gas bubbles from being formed and trapped between the sample support and the head of the probe. The presence of bubbles is undesirable as it can negatively affect the quality of the spectral data.

The head of the spectroscopic probe is typically wider than the sample support such that, when fully inserted into the cap, the probe does not enter the sample support, and the sample occupies the sample support and all or part of the groove(s). The groove(s) on the internal wall of the cap preferably extend from the sample support and up to the top of the cap to allow gases and excess liquid sample to leave the cell.

According to a preferred embodiment, after the insertion of the spectroscopic probe into the cap, the assembled cell is then transferred into an aluminium heating block where the cell is sealed using a stainless steel press. The whole cell—and hence the sample—is then heated and a spectrum is recorded.

The cell is preferably used for analysing the sample by infrared spectroscopy or NIR spectroscopy, more preferably NIR spectroscopy.

An advantage of the present invention is that the sample may be elevated to high temperatures and pressures without the loss of volatile substances. Suitably, inside the sample support the temperature is in the range of from 10° C. to 200° C. depending on the sample. For practical purposes a temperature slightly above ambient temperature, for example in the range of from 30° C. to 90° C., is most preferred. Temperatures and pressures outside of the stated limits are not excluded; however they do not fall under the preferred embodiments of the present invention.

Prior to the measurement of the sample of interest the pathlength of the cell may be measured by filling the cell with a standard solution, such as toluene, and measuring the spectrum. Preferably according to the present invention the pathlength of the probe is in the range of from 0.5 mm to 10 mm. The pathlength is defined by the distance that electromagnetic radiation travels through the sample before reaching the detector. Thus, where incident radiation passed from one optical fibre, through the sample in the sample support, reflects off the mirror, and passes back through the sample, then the pathlength will be twice the thickness of the portion of the sample located between the one or more optical fibres in the spectroscopic probe and the reflecting mirror.

According to the aforementioned process every time a different measurement is made the pathlength will vary, it is therefore advantageous to use a chemometric model which self-calibrates for varying pathlength. This said measurement of the pathlength for building the chemometric model may be done by the use of etalon fringes as disclosed in PCT application PCT/GB2006/000841, the contents of which are incorporated herein by reference.

The cap is preferably disposable to reduce the chances of contaminating subsequently analysed samples. The aforementioned preferred cap materials are particularly convenient in this regard due to their relatively low cost.

It is clear from the present invention that the probe claimed is preferably a DRIFTS probe. Nevertheless, according to the present invention it is the applicants' belief that it would be common knowledge for the man skilled in the art to use the aforementioned knowledge for any DRIFTS look alike probe, or even for an ATR probe. The present invention does not apply to a transflection probe.

BRIEF DESCRIPTION OF THE DRAWINGS

The invention is further illustrated by the attached figures, in which;

FIG. 1 is a longitudinal section through a DRIFTS cell in accordance with the present invention;

FIG. 2 is a longitudinal section through the same DRIFTS cell as illustrated in FIG. 1 after a 90° rotation about axis A-A';

FIG. 3 is a cross section of the removable cap of the DRIFTS cell illustrated in FIGS. 1 and 2.

DETAILED DESCRIPTION OF PREFERRED

Figure 4:
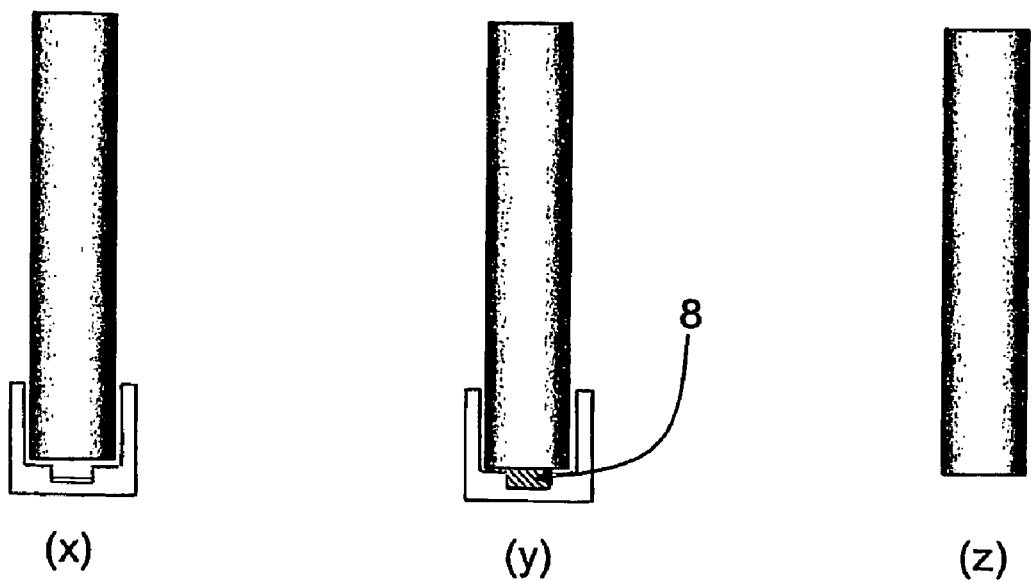
FIG. 4 shows a sequence of steps typically taken in order to collect a spectrum using the cell of the present invention.

FIG. 1 shows a DRIFTS cell comprising a probe 1 having two silica optical fibres 2 & 3. The head of the probe is inserted in a removable cap 4. The cap has a sample support 5 in the form of a circular depression in the base of the cap. In the base of the sample support is a reflecting mirror 6, which reflects radiation transmitted through a sample in the sample support back through the sample.

FIG. 2 shows the same DRIFTS cell as shown in FIG. 1, after a 90° rotation through axis A-A', in which a groove 7 is shown that connects the sample support with the top of the internal surface of the cap. FIG. 3 is a cross-section through axis B-B' of the removable cap 4 shown in FIGS. 1 and 2, showing the sample support 5 and reflecting mirror 6 in the base of the cap, and the groove 7 that connects the sample support with the internal wall of the cap.

FIG. 4 shows a sequence of steps by which a spectrum, for example a NIR spectrum, can be collected for a liquid sample using a cell according to the present invention. In step (x), a background spectrum is collected in which the sample support contains no sample. In step (y) sample 8 is added to the sample support in the same removable cap, the probe is inserted into the cap, and a spectrum of the sample is collected. The spectrum of the sample after background removal can then be calculated. In step (z), the removable cap is discarded, and the probe wiped clean, optionally with the aid of a suitable solvent.

The invention claimed is:

1. A sealable cell for measuring the electromagnetic spectrum of a liquid sample, which cell has a spectroscopic probe and a removable cap, which spectroscopic probe comprises a head and at least one optical fibre, and which removable cap can accommodate at least the head of the spectroscopic probe, and has a sample support with a reflecting mirror at its base, wherein the distance between the outer wall of the spectroscopic probe and the inner wall of the removable cap is less than 0.4 mm, and wherein the internal wall of the cap comprises at least one groove that allows a fluid to escape from between the head of the probe and the sample support when the probe is inserted into the removable cap.

2. A sealable cell according to claim 1, wherein the at least one groove on the internal wall of the cap extends from the sample support to the top of the cap.

3. A sealable cell according to claim 1, in which the internal wall of the cap is narrower than the outer wall of the spectroscopic probe.

4. A sealable cell according to claim 3, in which the cap is up to 0.4 mm narrower than the spectroscopic probe.

5. A sealable cell according to claim 1, in which the head of the spectroscopic probe is wider than the sample support.

6. A sealable cell according to claim 1, in which the spectroscopic probe and the cap are cylindrical, and the spectroscopic probe diameter is more than 1.5 mm and less than 30 mm.

7. A sealable cell according to claim 1, in which the removable cap is made from teflon, polypropylene or polyethylene.

8. A sealable cell according to claim 1, in which the cross sectional area of the groove is at least 0.1 mm.

9. A sealable cell according to claim 1, in which the reflecting mirror is made of aluminum.

10. A sealable cell according to claim 1, in which the spectroscopic probe comprises two silica optical fibres.

11. A sealable cell according to claim 1, wherein the probe is a DRIFTS probe or an ATR probe.

12. Method of performing a spectroscopic measurement on a liquid sample, comprising introducing the liquid into a sealable cell according to claim 1 and effecting the spectroscopic measurement on the sample.

13. Method according to claim 12, in which the liquid sample contains volatile substances.

14. Method according to claim 12, in which the spectroscopic measurements are NIR spectroscopic measurements.

15. Method according to claim 12, in which the liquid sample is crude oil, synthetic crude, a biocomponent, an intermediate stream, or blends of one or more thereof.

16. Method according to claim 15, in which the liquid sample is an intermediate stream selected from the group consisting of residue, gas oil, vacuum gas oil, naphtha, cracked stock, and blends of one or more thereof.

17. Method according to claim 12, in which the liquid sample is selected from the group consisting of fuels, lubricants, polymers (liquid polymers or polymer melts) and petrochemicals which are prone to fouling.

* * * * *